(12) United States Patent
Rool

(10) Patent No.: US 6,365,735 B1
(45) Date of Patent: Apr. 2, 2002

(54) VINCA-ALKALOID DERIVATIVES AND PREPARATION METHOD

(75) Inventor: Patrice Rool, Brunoy (FR)

(73) Assignee: Roowin S.A., Paris (FR)

( * ) Notice: Subject to any disclaimer, the term of this patent is extended or adjusted under 35 U.S.C. 154(b) by 0 days.

(21) Appl. No.: 09/701,502

(22) PCT Filed: Jun. 2, 1999

(86) PCT No.: PCT/FR99/01289

§ 371 Date: Jan. 8, 2000

§ 102(e) Date: Jan. 8, 2000

(87) PCT Pub. No.: WO99/62912

PCT Pub. Date: Dec. 9, 1999

(30) Foreign Application Priority Data

Jun. 2, 1998 (FR) .......................................... 98 06895

(51) Int. Cl.⁷ ............................................ C07D 519/04
(52) U.S. Cl. ...................................... 540/478; 540/579
(58) Field of Search ................................ 540/478, 579

(56) References Cited

U.S. PATENT DOCUMENTS

| | | | |
|---|---|---|---|
| 4,737,586 A | 4/1988 | Potier et al. | 540/478 |
| 5,037,977 A | 8/1991 | Tan et al. | |

FOREIGN PATENT DOCUMENTS

| | | |
|---|---|---|
| DE | 38 01 450 | 8/1988 |
| DE | 38 26 412 | 2/1989 |
| WO | WO 89/12056 | 12/1989 |
| WO | WO 89 12056 | 12/1989 |

OTHER PUBLICATIONS

Richard J. Sundberg et al.; "Mechanistic aspects of the formation of anhydrovinblastine by Potier–Polonovski oxidative coupling of catharanthine and vindoline. Spectroscopic observation and chemical reactions of intermediates" Tetrahedron., vol. 48, No. 2,—Jan. 10, 1992; pp. 277–296, XP002083507 Oxford GB—the whole document.

Richard J. Sundberg et al.; "Oxidative fragmentation of catharanthine by dichlorodicyanoquinone"; Journal of Organic Chemistry,—Mar. 1, 1991; pp. 1689–1692, XP002083508 Easton US —the whole document.

Richard J. Sundberg et al.; "Photoactivated C16–C21 fragmentation of catharanthine" Tetrahedron Letters, vol. 32, No. 26, Jun. 24, 1992, pp. 3035–3038 XP002083509 Oxford GB—the whole document.

E. Gunic et al., "Electrochemical Synthesis of Anhydrovinblastine", J. Chem. Soc., Chem. Commun., 1993, pp. 1496–1497.

I. Tabakovic et al., "Anodic Fragmentation of Catharanthine and Coupling with Vindoline. Formation of Anhydrovinblastine", J. Org. Chem., 1997, vol. 62, pp 947–953.

J. Vucovik et al., "Production of 3',4'–anhydrovinblastine: a Unique Chemical Synthesis", Pergamon Journals Ltd., 1988, vol. 44, pp. 325–331.

Primary Examiner—Richard L. Raymond
Assistant Examiner—Venkataraman Balasubramanian
(74) Attorney, Agent, or Firm—Henderson & Sturm LLP

(57) ABSTRACT

The invention concerns a novel method for preparing vinca-alkaloids by reacting a catharantine-type product and a vindoline-type product, characterized in that it consists in selecting the reaction conditions such that the product is oxidized.

24 Claims, No Drawings

VINCA-ALKALOID DERIVATIVES AND PREPARATION METHOD

SUMMARY

The invention relates to a new process for preparing vinca alkaloids by reacting a product of catharanthine and vindoline type, characterised in that the reaction conditions are chosen so that vindoline is oxidised.

The invention relates to a process for preparing vinca alkaloids of the general formula (I)

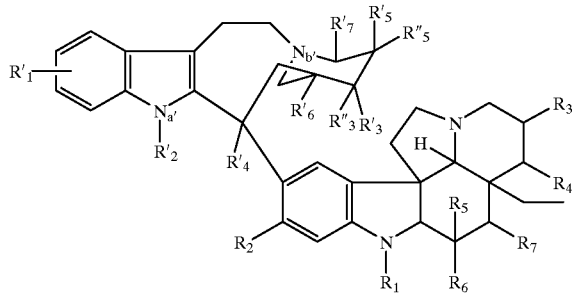

(I)

in which:

$R'_1$ represents a hydrogen atom or an alkoxy, acyl, formyl or halogenoacyl group, $R'_2$ represents a hydrogen atom or an alkyl group, $R'_3$ and $R''_3$ are identical or different and each independently represents a hydrogen atom or a hydroxyl or alkanoyloxyl group, or else $R'_3$ and $R''_3$ together form a carbonyl group or else $R'_3$ and $R'_5$ together form an epoxy bridge or a double bond, $R'_4$ represents a hydrogen atom or an alkyloxycarbonyl, hydroxymethyl or alkanoyloxymethyl group, preferably an alkyloxycarbonyl group, $R'_5$ and $R''_5$ are identical or different and each independently represents a hydrogen atom or a hydroxyl, alkanoyloxyl, ethyl or 2-hydroxyethyl group, $R'_6$ represents a hydrogen atom or an ethyl, 2-hydroxyethyl or acetyl group, $R'_7$ represents a hydrogen atom or a cyanide group, $R_1$ represents a hydrogen atom or an alkyl, formyl or acyl group, preferably hydrogen or an alkyl group, $R_2$ represents a hydrogen atom or an alkoxy group, $R_3$ represents a hydrogen atom or a hydroxyl or alkanoyloxyl group, or else $R_3$ and $R_4$ together form an epoxy bridge or a double bond, $R_4$ represents a hydrogen atom or a hydroxyl or alkanoyloxyl group, or else $R_4$ and $R_5$ together form an epoxy bridge, $R_6$ represents an alkyloxycarbonyl, hydrazido, acetamido, hydroxymethyl or alkanoyloxymethyl group, $R_5$ and $R_7$ represent a hydrogen atom or a hydroxyl or alkanoyloxyl group, as well as their addition salts with acids and their quaternary ammonium salts.

Some derivatives of the formula (I) are known as being intermediates in the preparation of anti-tumor medicaments such as vinblastine, vincristine and vinorelbine.

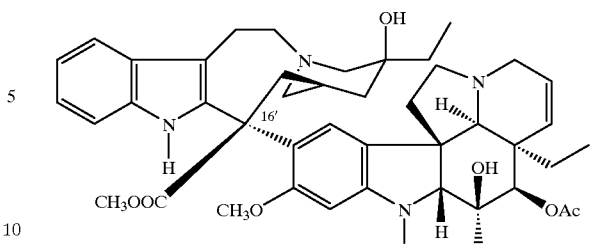

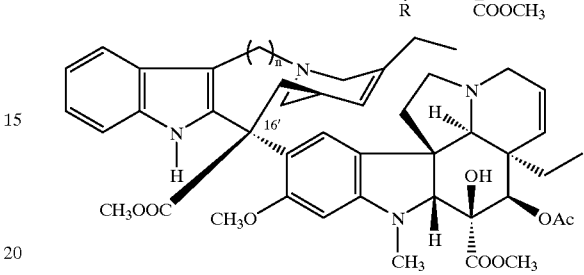

$R=CH_3$, vinblastine
$R=CHO$, vincristine
$n=2$, anhydrovinblastine
$n=1$, vinorelbine The remarkable anti-tumor properties of these complex natural molecules, extracted from the Madagascar periwinkle, *Carantheus roseus*, are known and they are already used in anti-cancer treatment. Vinblastine and vincristine are "spindle poisons" which oppose the formation of the mitotic spindle during cellular division, thus preventing cellular proliferation.

Vincristine and vinblastine are active agents in the treatment of leukemia, lymphosarcoma and solid tumors. Vinblastine is also used in the treatment of Hodgkin's disease.

Vinorelbine is currently used in the treatment of the most widespread form of cancer of the lungs, that is lung cancer of non-small cells. It is also used in the treatment of metastasic cancers of the breast.

The methods currently used for preparing vinblastine and vincristine involve extraction of these molecules from plants. The plants have to be crushed and dried before these substances can be extracted. The extraction process is long and costly, given that the extract obtained is very complex, containing at least 200 different alkaloids. The yields are also very low; 5 to 10 g of vinoblastine are obtained per ton of dried plant material, and 0.5 to 1 g of vincristine per ton of dried plant material.

Many research groups have thus tried to achieve synthesis of these molecules by using more efficient procedures which enable better yields and which make use of derivatives with interesting anti-tumor properties but which are endowed with lower levels of toxicity.

The patent FI 882 755, filed by the HUATAN-MAKI Oy Company, relates to the formation of vinblastine and vincristine by irradiation of catharanthine and of vindoline with UV radiation in an acidic aqueous solution, under an atmosphere of oxygen or an inert gas. The yields obtained in these reactions are extremely low.

Furthermore, other processes are known which make use of anhydrovinblastine which is an intermediate in the synthesis of vinblastine, vincristine and also of vinorelbine.

Anhydrovinblastine is thus a key chemical intermediate which enables access to all alkaloids of the vinblastine type. This intermediate is synthesised by coupling catharanthine and vindoline.

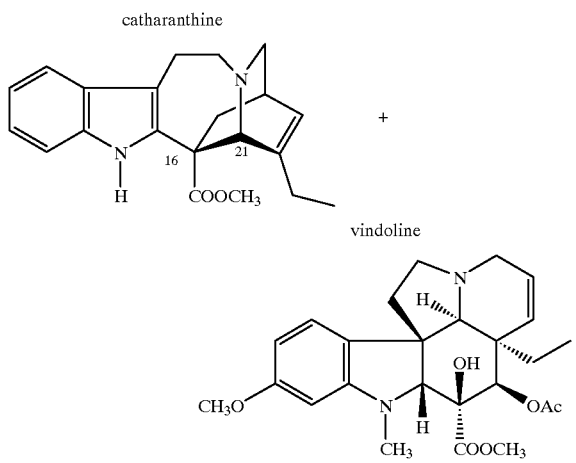

The latter two alkaloids are also extracted from the Madagascar periwinkle but, in contrast to vincristine and vinblastine, they represent the main constituents of the extract obtained. In fact, 400 g of catharanthine per ton of dried plant material and 800 g of vindoline per ton of dried plant material are obtained.

The preparation of anhydrovinblastine by coupling catharanthine and vindoline is therefore a favoured route for synthesising this intermediate product.

There are several methods for preparing anhydrovinblastine from catharanthine and vindoline.

The patent FR 2 296 418 filed by ANVAR describes a process during the course of which the N-oxide of catharanthine is coupled to vindoline in the presence of trifluoroacetic anhydride.

When this process is performed at ambient temperature only the inactive 16'-R epimer of anhydrovinblastine is obtained. The naturally occurring active 16'-S epimer is obtained as the major product when this reaction is performed at a temperature which is at least 50° C. lower and under an inert gas. Nevertheless, even at low temperature, 10% of the 16'-R epimer of anhydrovinblastine is still produced.

This process has several disadvantages. The operating conditions are extremely restrictive due to the use of anhydrous solvents, the low temperature and the atmosphere of inert gas. The product obtained has to be subjected to a purification procedure due to the presence of 10% of the 16'-R epimer of anhydrovinblastine. The yield of isolated anhydrovinblastine is low, of the order of 35%.

A second process, suggested by VUKOVIC et al. in the review "Tetrahedron" (1998, volume 44, pages 325–331) describes a coupling reaction between catharanthine and vindoline initiated by ferric ions. Catharanthine is also oxidised in this reaction. The yield of anhydrovinblastine is of the order of 69% when the reaction is performed under an atmosphere of inert gas. However, this process has the major disadvantage that it leads to many secondary products. These are impurities resulting from further oxidation of the dimeric alkaloids formed, whatever the chosen operating conditions. This makes the purification stage difficult and delicate.

An improved process was suggested in the patent U.S. Pat. No. 5,037,977 and this increases the yield of anhydrovinblastine to 89%. However, this improvement is described only for very small amounts of reagents and its extension to the industrial scale seems to be difficult. In any case, these processes based on ferric ions lead in all cases to many secondary products due to the fact that these ions are responsible for parasitic reactions.

A third process described by GUNIC et al. in "Journal of the Chemical Society Chemical Communications" (1993), volume 19, pages 1496–1497, and by Tabakovic et al. in "Journal of Organic Chemistry" (1997), volume 62, pages 947–953, describes a coupling reaction between catharanthine and vindoline as a result of anodic oxidation of catharanthine. However, this process also suffers from disadvantages which, on the one hand, are due to the requirement for an inert atmosphere and, on the other hand, are connected with the nature of the electrochemical process itself, involving wear of the electrodes, difficulty in controlling the reproducibility and the cost of electrolytes. And, as in all the preceding methods, the anhydrovinblastine is contaminated with about 10% of the 16'-R epimer of anhydrovinblastine.

It should be noted that all the processes disclosed hitherto, without exception, involve splitting open the catharanthine molecule, this being induced by oxidation or activation of the latter. These processes are performed under restrictive conditions and do not permit satisfactory yields of a sufficiently pure product.

The process according to the invention permits the production of vinca alkaloids of the general formula (I) and in particular of anhydrovinblastine, by making use of less restrictive operating conditions, with excellent yields and high purity. The process according to the invention permits the production of anhydrovinblastine in its naturally occurring active form, without any trace of the 16'-R epimer of anhydrovinblastine.

The present invention thus relates to a process for preparing a product (A) corresponding to the general formula (I)

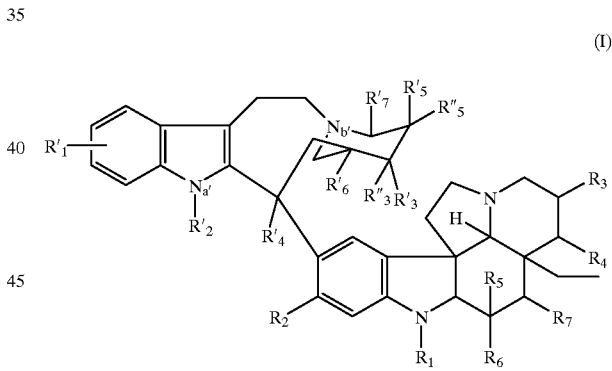

in which:
R'$_1$ represents a hydrogen atom or an alkoxy, acyl, formyl or halogenoacyl group, R'$_2$ represents a hydrogen atom or an alkyl group, R'$_3$ and R''$_3$ are identical or different and each independently represents a hydrogen atom or a hydroxyl or alkanoyloxyl group, or else R'$_3$ and R''$_3$ together form a carbonyl group, or else R'$_3$ and R'$_5$ together form an epoxy bridge or a double bond, R'$_4$ represents a hydrogen atom or an alkyloxycarbonyl, hydroxymethyl or alkanoyloxymethyl group, preferably an alkyloxycarbonyl group, R'$_5$ and R''$_5$ are identical or different and each independently represent a hydrogen atom or a hydroxyl, alkanoyloxyl, ethyl or 2-hydroxyethyl group, R'$_6$ represents a hydrogen atom or an ethyl, 2-hydroxyethyl or acetyl group, R'$_7$ represents a hydrogen atom or a cyanide group, R$_1$ represents a hydrogen atom or an alkyl, formyl or acyl group, preferably hydrogen or an alkyl group, R$_2$ represents a hydrogen atom or an alkoxy group, R$_3$ represents a hydrogen atom or a hydroxyl or alkanoyloxyl group, or else R$_3$ and R$_4$ together form an epoxy bridge or a double bond, R$_4$ represents a hydrogen atom or a hydroxyl or alkanoyloxyl group, or else R$_4$ and R$_5$ together form an epoxy bridge, R$_6$ represents an alkyloxycarbonyl, hydrazido, acetamido, hydroxymethyl or alkanoyloxymethyl group, R$_5$ and R$_7$ represent a hydrogen atom or a hydroxyl or alkanoyloxyl group, as well as their addition salts with acids and their quaternary ammonium salts, by reacting a product (c) corresponding to the general formula (II):

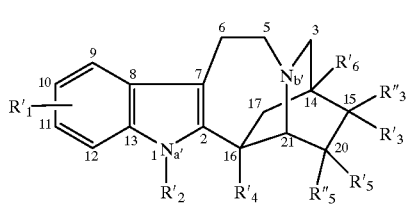

in which R'$_1$, R'$_2$, R'$_3$, R''$_3$, R'$_4$, R'$_5$, R''$_5$ and R'$_6$ are defined as above, with a product (v) corresponding to the general formula (III):

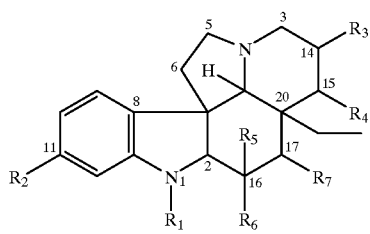

in which R$_1$, R$_2$, R$_3$, R$_4$, R$_5$, R$_6$ and R$_7$ are defined as above, this process being characterised in that the reaction conditions are chosen such that product (v) is oxidised in order to obtain an intermediate (i) of the general formula (IV):

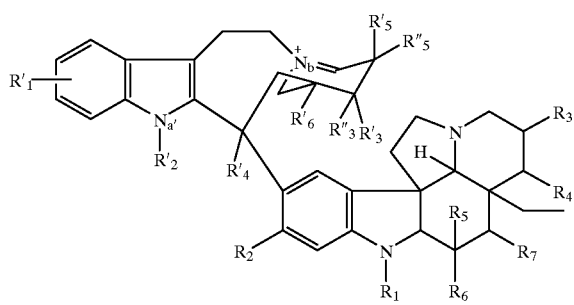

in which R$_1$, R$_2$, R$_3$, R$_4$, R$_5$, R$_6$ R$_7$ and R'$_1$, R'$_2$, R'$_3$, R''$_3$, R'$_4$, R'$_5$, R''$_5$ and R'$_6$ are defined as above, and in that the product (i) of formula (IV) is subjected either to reduction or to cyanation in order to obtain product (A) of formula (I).

Product (v) can be oxidised using any known means. The following may be mentioned by way of example: photochemical, organometallic and electrochemical routes. Product (v) is preferably oxidised using the photochemical route in the presence of light and optionally an organic or inorganic sensitizer.

The inorganic sensitizer may be a transition metal or a semi-conductor, preferably being a ruthenium complex or titanium oxide.

The organic sensitizer is a colorant, preferably chosen from the group consisting of xanthates, pyriliums, pyridiniums, flavines, aromatic compounds, ketones and quinones as well as their salts, in particular chosen from among fluorescein, triphenylpyrilium, 4-(4-methoxyphenyl)-2,6-diphenylpyrilium, 2,6-bis-(4-methoxyphenyl)-4-phenyl-pyrilium and 2,4,6-tris-(4-methoxyphenyl)-pyrilium.

The oxidation step is performed in an acidic medium, preferably at a pH between 0 and 7, in particular between 0.5 and 3.

The reduction stage for product (i) may be performed by any known means. An alkaline borohydride is preferably used, in particular sodium borohydride.

The cyanation step for product (i) may be performed by any known means. This step is preferably performed in an organic medium in the presence of a source of cyanide ions which are not alkaline, or are slightly alkaline, in particular in the presence of trimethylsilyl cyanide.

In fact, the applicant Company has discovered that choosing the reaction conditions in such a way as to oxidise product (v) (and not product (c) as in the prior art), leads to a stereospecific reaction with respect to the C$_{16}$ carbon atom in intermediate (i), thus avoiding contamination by the inactive 16'-R epimer. Moreover, this stereospecificity is independent of the temperature of the reaction medium, thus simplifying the method of preparation.

When (v) is oxidised via the photochemical route, the light used is within the UV/visible spectrum, preferably greater than 254 nm and in particular greater than 400 nm.

The invention also relates to a process for preparing anhydrovinblastine by reacting catharanthine with vindoline, this process being characterised in that the reaction conditions are chosen in such a way that vindoline is oxidised in order to obtain an intermediate (i') of the formula (V):

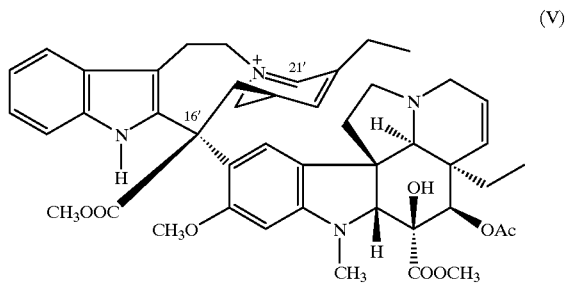

and in that the intermediate (i') of formula (V) is subjected to reduction in order to obtain anhydrovinblastine.

The invention also relates to novel products (B), corresponding to formula (VI):

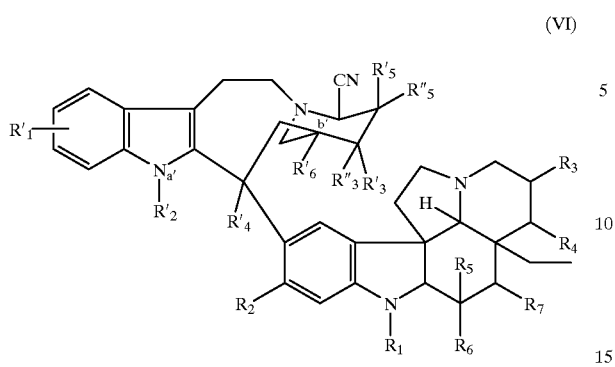

(VI)

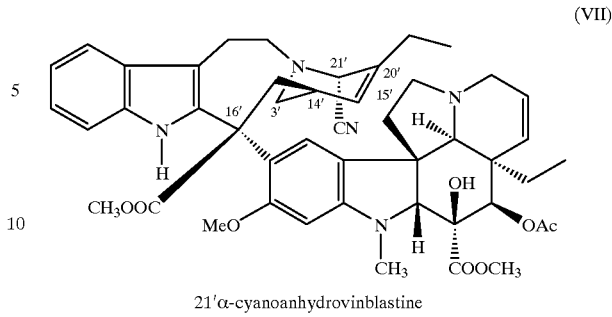

(VII)

21′α-cyanoanhydrovinblastine in which:

R′$_1$ represents a hydrogen atom or an alkoxy, acyl, formyl or halogenoacyl group, R′$_2$ represents a hydrogen atom or an alkyl group, R′$_3$ and R″$_3$ are identical or different and each independently represents a hydrogen atom or a hydroxyl or alkanoyloxyl group, or else R′$_3$ and R″$_3$ together form a carbonyl group, or else R″$_3$ and R′$_5$ together form a double bond, R′$_4$ represents a hydrogen atom or an alkyloxycarbonyl, hydroxymethyl or alkanoyloxymethyl group, R′$_5$ and R″$_5$ are identical or different and each independently represents a hydrogen atom or a hydroxyl, alkanoyloxyl, ethyl or 2-hydroxyethyl group, R′$_6$ represents a hydrogen atom or an ethyl, 2-hydroxyethyl or acetyl group, R$_1$ represents a hydrogen atom or an alkyl, formyl or acyl group, R$_2$ represents a hydrogen atom or an alkoxy group, R$_3$ represents a hydrogen atom or a hydroxyl or alkanoyloxyl group, or else R$_3$ and R$_4$ together form an epoxy bridge or a double bond, R$_4$ represents a hydrogen atom or a hydroxyl or alkanoyloxyl group, or else R$_4$ and R$_5$ together form an epoxy bridge, R$_6$ represents an alkyloxycarbonyl, hydrazido, acetamido, hydroxymethyl or alkanoyloxymethyl group, R$_5$ and R$_7$ represent a hydrogen atom or a hydroxyl or alkanoyloxyl group.

These are new derivatives of vinca alkaloids in which there is a cyanide group attached to the carbon in position 21′. These products have the advantage of being readily functionalised, thus enabling the production of new molecules which are of potential interest at the cytotoxic level.

These products (B) can be functionalised either by nucleophilic compounds or by electrophilic compounds.

In addition, the invention relates to a new product (D) of the formula VII:

This is a derivative of anhydrovinblastine, that is to say 21′α-cyanoanhydrovinblastine. In fact, the applicant Company has developed a process for manufacturing 21′α-cyanoanhydrovinblastine, a molecule which can readily be functionalised and thus permits the production of novel derivatives which are of potential interest at the cytotoxic level.

21′a-cyanoanhydrovinblastine can be functionalised either by nucleophilic compounds or by electrophilic compounds. Thus, the range of potentially accessible derivatives is very large.

This new compound (D) is also very interesting because it is relatively stable, which enables it to be isolated and obtained in the pure, crystalline form. The advantage of obtaining crystals of a precursor of derivatives is that functionalisation reactions of this precursor can be performed in a clean reaction medium, free of all traces of reactive residues.

21′α-cyanoanhydrovinblastine enables the production of derivatives which are mono or polysubstituted at positions C$_{15′}$, C$_{20′}$ and C$_{21′}$ in anhydrovinblastine or these derivatives.

The invention also relates to a process for preparing 21′α-cyanoanhydrovinblastine by reacting catharanthine with vindoline, this process being characterised in that the reaction conditions are chosen in such a way that vindoline is oxidised in order to obtain an intermediate (i′) of the formula (V) and in that the intermediate (i′) is subjected to cyanation in order to obtain product (D).

Cyanation is preferably performed in an organic medium in the presence of a source of cyanide ions which are not alkaline, or are slightly alkaline, for example trimethylsilyl cyanide.

The invention will be better understood with the aid of the non-restrictive examples which follow.

EXAMPLE 1

0.473 mmol of catharanthine hydrochloride (176 mg), 0.473 mmol of vindoline (216 mg) and 0.473 mmol of triphenylpyrilium hydrogen sulfate (192 mg) are added to 25 ml of 0.1 N hydrochloric acid. The entire mixture is irradiated with light of wavelength λ>400 nm in a Pyrex irradiation flask, under an atmosphere of oxygen. After irradiating for 6 h 30 min, the medium is extracted with dichloromethane.

The aqueous phase is then reduced at 0° C. using an excess of sodium borohydride (2 eq.) dissolved in 3 ml of molar sodium carbonate, added dropwise. The reaction medium is then extracted with dichloromethane, dried and evaporated under reduced pressure at 20° C. The residue is solubilised in 0.5 N hydrochloric acid and washed with diethyl ether. The aqueous phase is made alkaline by adding ammonia and extracted with dichloromethane.

The only product in the residue (337 mg, 0.426 mmol, 90%) is recrystallised from absolute ethanol. 290 mg of white crystals of anhydrovinblastine (0.366 mmol; yield: 77%) are recovered.

EXAMPLE 2

0.537 mmol of catharanthine hydrochloride (200 mg), 0.537 mmol of vindoline (245 mg), 0.054 mmol of dimethyl viologen (14 mg) and 0.026 mmol of triphenylpyrilium hydrogen sulfate (11 mg) are added to 50 ml of 0.1 N sulfuric acid. The entire mixture is irradiated with light of wavelength $\lambda > 400$ nm in a Pyrex irradiation flask, under an atmosphere of oxygen. The reaction is terminated after irradiating for 2 h 30 min.

The aqueous phase is then reduced at 0° C. with an excess of sodium borohydride (2 eq.) dissolved in 10 ml of molar sodium carbonate, added dropwise. The reaction mixture is then extracted with dichloromethane, dried and evaporated under reduced pressure at 20° C. The residue is solubilised in 0.5 N hydrochloric acid and washed with diethyl ether. The aqueous phase is made alkaline using ammonia and extracted with dichloromethane.

The only product in the residue (403 mg, 0.509 mmol, 95%) is recrystallised from absolute ethanol. 340 mg of white crystals of anhydrovinblastine (0.430 mmol; yield: 80%) are recovered.

EXAMPLE 3

0.537 mmol of catharanthine hydrochloride (200 mg), 0.537 mmol of vindoline (245 mg) and 0.054 mmol of 2,6-bis-(4-methoxyphenyl)-4-phenylpyrilium hydrogen sulfate (25 mg) are added to 50 ml of 0.1 N sulfuric acid. The entire mixture is irradiated with light of wavelength $\lambda > 400$ nm in a Pyrex irradiation flask, under an atmosphere of oxygen. The reaction is terminated after 2 hours of irradiation.

The aqueous phase is then reduced at 0° C. using an excess of sodium borohydride (2 eq.) dissolved in 10 ml of molar sodium carbonate, added dropwise. The reaction mixture is then extracted with dichloromethane, dried and evaporated under reduced pressure at 20° C. The residue is solubilised in 0.5 N hydrochloric acid and washed with diethyl ether. The aqueous phase is made alkaline with ammonia and extracted with dichloromethane.

The only product in the residue (408 mg, 0.516 mmol, 96%) is recrystallised from absolute ethanol. 340 mg of white crystals of anhydrovinblastine (0.430 mmol; yield: 80%) are recovered.

EXAMPLE 4

0.806 mmol of catharanthine hydrochloride (300 mg), 0.806 mmol of vindoline (367 mg) and 0.040 mmol of fluorescein (5%) are added to 50 ml of 0.1 N sulfuric acid. The entire mixture is irradiated with light of wavelength $\lambda > 400$ nm in a Pyrex irradiation flask, under an atmosphere of oxygen. The reaction is terminated after 3 hours of irradiation.

The aqueous phase is then reduced at 0° C. using an excess of sodium borohydride (2 eq.) dissolved in 3 ml of molar sodium carbonate, added dropwise. The reaction mixture is then extracted with dichloromethane, dried and evaporated under reduced pressure at 20° C.

The only product in the residue (613 mg, 0.774 mmol, 96%) is recrystallised from absolute ethanol. 523 mg of white crystals of anhydrovinblastine (0.661 mmol; yield: 82%) are recovered.

EXAMPLE 5

0.268 mmol of catharanthine hydrochloride (100 mg), 0.268 mmol of vindoline (122 mg) and 0.029 mmol (5%) of the sodium salt of riboflavine-5'-phosphate dihydrate (FMN) are added to 50 ml of 0.1 N hydrochloric acid. The entire mixture is irradiated with light of wavelength $\lambda > 400$ nm in a Pyrex irradiation flask, under an atmosphere of oxygen. The reaction is terminated after 4 hours of irradiation.

The aqueous phase is then reduced at 0° C. using an excess of sodium borohydride (2 eq.) dissolved in 3 ml of molar sodium carbonate, added dropwise. The reaction mixture is then extracted with dichloromethane, dried and evaporated under reduced pressure at 20° C.

After recrystallisation from absolute ethanol of the only product in the residue (171 mg, 0.216 mmol, 80%), 140 mg of white crystals of anhydrovinblastine (0.176 mmol; yield: 66%) are recovered.

EXAMPLE 6

0.577 mmol of catharanthine hydrochloride (215 mg), 0.577 mmol of vindoline (263 mg) and 0.029 mmol (5%) of the dichloride of N,N'-dimethyl-2,7-diazapyrenium (DAP) are added to 60 ml of 0.1 N hydrochloric acid. The entire mixture is irradiated with light of wavelength $\lambda > 400$ nm in a Pyrex irradiation flask, under an atmosphere of oxygen. The reaction is terminated after 3 h 30 min of irradiation.

The aqueous phase is then reduced at 0° C. using an excess of sodium borohydride (2 eq.) dissolved in 3 ml of molar sodium carbonate, added dropwise. The reaction mixture is then extracted with dichloromethane, dried and evaporated under reduced pressure at 20° C.

After purification of the residue (379 mg, 0.479 mmol, 83%) by flash chromatography on silica gel and recrystallisation from absolute ethanol, 274 mg of white crystals of anhydrovinblastine (0.346 mmol; yield: 60%) are recovered.

EXAMPLE 7

0.357 mmol of catharanthine hydrochloride (120 mg), 0.357 mmol of vindoline (152 mg) and 2 g of $TiO_2$ are added to 25 ml of 0.1 N hydrochloric acid. The entire mixture is irradiated with light of wavelength $\lambda > 345$ nm in a Pyrex irradiation flask, under an atmosphere of oxygen. After 2 hours of irradiation, the medium is extracted with dichloromethane.

The aqueous phase is then reduced at 0° C. using an excess of sodium borohydride (2 eq.) dissolved in 3 ml of molar sodium carbonate, added dropwise. The reaction mixture is then extracted with dichloromethane, dried and evaporated under reduced pressure at 20° C.

After purification by flash chromatography on silica gel, 85 mg of anhydrovinblastine (0.107 mmol; yield: 30%) are obtained.

EXAMPLE 8

0.448 mmol of catharanthine hydrochloride (166 mg), 0.448 mmol of vindoline (204 mg) and a catalytic amount (5%) of rhodamine 6G are added to 60 ml of 0.1 N sulfuric acid. The entire mixture is irradiated with light of wavelength $\lambda > 400$ nm in a Pyrex irradiation flask, under an atmosphere of oxygen. After 3 h 30 min of irradiation, the medium is extracted with dichloromethane.

The aqueous phase is then reduced at 0° C. using an excess of sodium borohydride (2 eq.) dissolved in 3 ml of molar sodium carbonate, added dropwise. The reaction mixture is then extracted with dichloromethane, dried and evaporated under reduced pressure at 20° C.

After purification by flash chromatography, 124 mg of anhydrovinblastine (0.157 mmol; yield: 35%) are obtained.

EXAMPLE 9

0.537 mmol of catharanthine hydrochloride (200 mg), 0.537 mmol of vindoline (245 mg) and 0.054 mmol of dimethyl viologen (14 mg) are added to 50 ml of 0.1 N hydrochloric acid. The entire mixture is irradiated with light of wavelength λ>360 nm in a Pyrex irradiation flask, under an atmosphere of oxygen. The reaction is terminated after 2 hours of irradiation.

The aqueous phase is then reduced at 0° C. using an excess of sodium borohydride (2 eq.) dissolved in 3 ml of molar sodium carbonate, added dropwise. The reaction mixture is then extracted with dichloromethane, dried and evaporated under reduced pressure at 20° C.

The only product in the residue (391 mg, 0.494 mmol, 92%) is recrystallised from absolute ethanol. 345 mg of white crystals of anhydrovinblastine (0.435 mmol; yield: 81%) are recovered.

EXAMPLE 10

0.537 mmol of catharanthine hydrochloride (200 mg) and 0.537 mmol of vindoline (245 mg) are added to 50 ml of 0.1 N hydrochloric acid. The entire mixture is irradiated with light of wavelength λ>360 nm in a Pyrex irradiation flask, under an atmosphere of oxygen. The reaction is terminated after 2 hours of irradiation.

The aqueous phase is then reduced at 0° C. using an excess of sodium borohydride (2 eq.) dissolved in 3 ml of molar sodium carbonate, added dropwise. The reaction mixture is then extracted with dichloromethane, dried and evaporated under reduced pressure at 20° C.

The only product in the residue (383 mg, 0.483 mmol, 90%) is recrystallised from absolute ethanol. 332 mg of white crystals of anhydrovinblastine (0.419 mmol; yield: 78%) are recovered.

EXAMPLE 11

Preparation of 21'α-Cyanoanhydrovinblastine 0.537 mmol of catharanthine hydrochloride (200 mg), 0.537 mmol of vindoline (245 mg) and 0.054 mmol of dimethyl viologen (14 mg) and 0.028 mmol of triphenylpyrilium hydrogen sulfate (11 mg) are added to 50 ml of 0.1 N sulfuric acid. The entire mixture is irradiated with light of wavelength λ>400 nm in a Pyrex irradiation flask, under an atmosphere of oxygen. The reaction is terminated after 2 h 30 min of irradiation.

The aqueous phase is then saturated with lithium tetrafluoroborate and then extracted with dichloromethane. A solution of 15 ml of dichloromethane containing 100 μl (1.34 mmol, 2 eq.) of trimethylsilyl cyanide, TMSCN, is then added to the reaction medium. The organic phase is washed with a solution of 0.1 M sodium carbonate, dried and evaporated under reduced pressure at 20° C.

The only product in the residue (403 mg, 0.509 mmol, 95%) is recrystallised from absolute isopropanol. 340 mg of white crystals of 21'α-cyanoanhydrovinblastine (0.430 mmol; yield: 80%) are recovered.

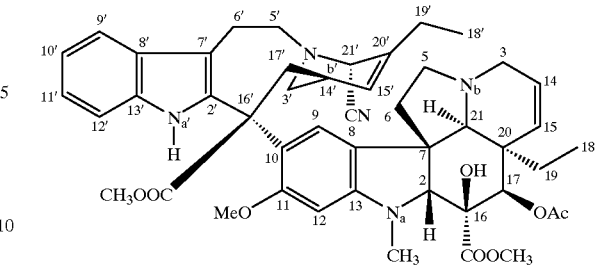

$C_{47}H_{55}N_5O_8$

M.pt. 212° C. (iPrOH) IR film 3450, 2950, 2220, 1740, 1610 cm$^{-1}$; MS M/z (relative intensity) 818 (MH+, 3), 122 (100), 108 (21);

NMR $^1$H (500 MHz, CDCl3) 9.78 (s, 1H, OH), 8.04 (s, 1H, Na'H), 7.51 (1H, H-9'), 7.16 (1H, H-11'), 7.13 (1H, H-12'), 7.12 (1H, H-10'), 6.63 (s, 1H, H-9), 6.13 (s, 1H, H-12), 5.85 (m, 1H, H-14), 5.47 (s, 1H, H$_\alpha$-17), 5.54 (m, 1H, H-15'), 5.30 (m 1H, H-15), 4.18 (1H, H$_{62}$-2), 3.60 (s, 3H, C16'—COOCH$_3$), 3.38 (1H, H$_{62}$-3), 3.35 (1H, H$_\beta$-3'), 3.31 (1H, H$_\beta$-5), 3.25 (1H, H$_\beta$-6'), 3.24 (m, 1H, H$_\beta$-5'), 3.15 (1H, H$_\beta$-17'), 3.14 (m, 1H, H$_\alpha$-5'), 3.12 (1H, H$_\alpha$-6'), 2.82 (1H, H$_\alpha$-3), 2.72 (s, 3H, NaCH$_3$), 2.66 (s, 1H, H$_\alpha$-21), 2.62 (1H, H$_\alpha$-3'), 2.46 (1H, H$_\alpha$-5), 2.40 (1H, H$_\alpha$-17'), 2.20 (1H, H$_\beta$-5), 2.11 (s, 3H, CH$_3$—COO), 2.11 (1H, H-19'), 2.03 (1H, H-19'), 1.80 (1H, H$_\alpha$-6), 1.80 (1H, H-19), 1.35 (1H, H-19), 1.21 (m, 1H, H-14'), 1.04 (3H, H-18'), 0.81 (3H, H-18).

NMR $^{13}$C (125 MHz, CDCl3) 174.69 (C$_{16'}$—$\underline{C}$OOCH$_3$), 171.74 (C$_{16}$—$\underline{C}$OOCH$_3$), 171.03130.01 (C$_{15}$), 129.34 (C$_{8'}$), 129.16 (C$_{15'}$), 124.63 (C$_{14}$), 123.48 (C$_9$), 123.24 (C$_8$), 122.49 (C$_{11'}$), 121.00 (C$_{10}$), 119.21 (C$_{10'}$), 119.21 (CN), 118.35 (C$_{9'}$), 115.65 (C$_{7'}$), 110.64 (C$_{11}$—O$\underline{C}$H$_3$), 55.40 (C$_{16'}$), 53.30 (C$_7$), 52.46 (C$_{16'}$—COO$\underline{C}$H$_3$), 52.30 (C$_{16}$—COO$\underline{C}$H$_3$), 52.26 (C$_{5'}$), 50.50 (C$_5$), 50.41 (C$_5$), 44.86 (C$_6$), 44.48 (C$_3$), 42.76 (C$_{20}$), 38.32 (Na—CH$_3$), 34.00 (C$_{17}$), 33.28 (C$_{14'}$), 30.92 (C$_{19}$), 28.63 (C$_{8'}$), 25.92 (C$_{19'}$), 21.19 ($\underline{C}$H$_3$—COO), 11.86 (C$_{18'}$), 8.50 (C$_{18}$).

What is claimed is:

1. A process for preparing a product (A) corresponding to the compound of formula (I),

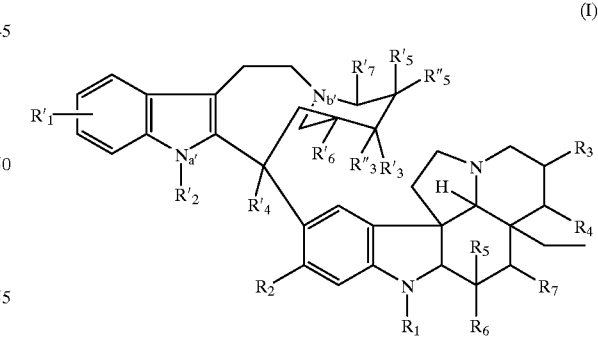

(I)

in which:

R'$_1$ represents a hydrogen atom or an alkoxy, acyl, formyl or halogenoacyl group, R'$_2$ represents a hydrogen atom or an alkyl group, R'$_3$ and R"$_3$ are identical or different and each independently represents a hydrogen atom or a hydroxyl or alkanoyloxyl group, or R'$_3$ and R"$_3$ together form a carbonyl group, or R'$_3$ and R'$_5$ form an epoxy bridge or a double bond, R'₄ represents a hydrogen atom or an alkyloxycarbonyl, hydroxymethyl or alkanoyloxymethyl group, R'₅ and R"₅ are identical or different and each independently represents a hydrogen atom or a hydroxyl, alkanoyloxyl, ethyl or 2-hydroxyethyl group, R'₆ represents a hydrogen atom or an ethyl, 2-hydroxyethyl or acetyl group, R'₇ represents a hydrogen atom or a cyanide group, R₁ represents a hydrogen atom or an alkyl, formyl or acyl group, preferably hydrogen or an alkyl group, R₂ represents a hydrogen atom or an alkoxy group, R₃ represents a hydrogen atom or a hydroxyl or alkanoyloxyl group, or R₃ or R₄ together form an epoxy bridge or a double bond, R₄ represents a hydrogen atom or a hydroxyl or alkanoyloxyl group, or R₄ and R₅ together form an epoxy bridge, R₆ represents an alkyloxycarbonyl, hydrazido, acetamido, hydroxymethyl or alkanoyloxymethyl group, R₅ and R₇ represent a hydrogen atom or a hydroxyl or alkanoyloxyl group, as well as their addition salts with acids and their quaternary ammonium salts by reacting a product (c) corresponding to the compound of formula (II):

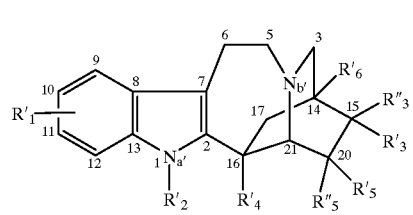

(II)

in which R'₁, R'₂, R'₃, R"₃, R'₄, R'₅, R"₅ and R'₆ are defined as above, with a product (v) corresponding to the compound of formula (III):

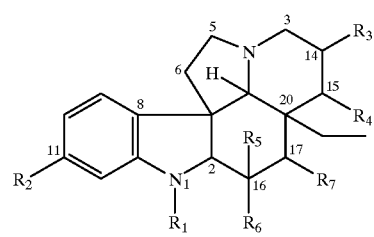

(III)

in which R₁, R₂, R₃, R₄, R₅, R₆ and R₇ are defined as above, wherein the reaction conditions are chosen such that product (v) is oxidized in order to obtain a product (i) of formula (IV):

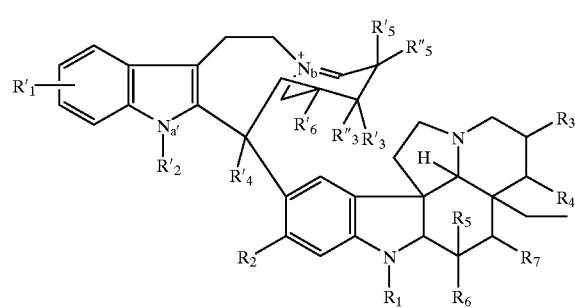

(IV)

in which R₁, R₂, R₃, R₄, R₅, R₆ R₇ and R'₁, R'₂, R'₃, R"₃, R'₄, R'₅, R"₅ and R'₆ are defined as above, and wherein the product (i) of formula (IV) is subjected either to reduction or to cyanation in order to obtain product (A).

2. The process according to claim 1, wherein R'₄ represents an alkyloxycarbonyl group.

3. The process according to claim 1, wherein the product (v) is oxidized by a photochemical route.

4. The process according to claim 1, wherein the product (v) is oxidized by an organometallic route.

5. The process according to claim 1, wherein the product (v) is oxidized by an electrochemical route.

6. The process according to claim 3, wherein oxidation by the photochemical route is performed in the presence of light.

7. The process according to claim 6, wherein oxidation by the photochemical route is performed in the presence of light and of the inorganic sensitizer selected from a transition metal or a semiconductor.

8. The process according to claim 7, wherein the transition metal is selected from a ruthenium complex or a titanium oxide.

9. The process according to claim 6, wherein oxidation by the photochemical route is performed in the presence of light and of an organic sensitizer which is a colorant selected from the group consisting of fluorescein, triphenylpyrilium, 4-(4-methoxyphenyl)-2,6-diphenylpyrilium, 2,6-bis-(4-methoxyphenyl)-4-phenylpyrilium and 2,4,6-tris-(4-methoxyphenyl)-pyrilium.

10. The process according to claim 6, wherein the light has a wavelength in the UV/visible spectrum.

11. The process according to claim 10, wherein the light has a wavelength in the UV/visible spectrum greater than 254 nm.

12. The process according to claim 10, wherein the light has a wavelength in the UV/visible spectrum greater than 400 nm.

13. The process according to claim 1, wherein the reduction step is performed with the aid of an alkaline borohydride.

14. The process according to claim 13, wherein the reduction step is performed with the aid of sodium borohydride.

15. The process according to claim 1, wherein the product (A) is anhydrovinblastine, (c) is catharanthine, (v) is vindoline, and the product (i) corresponds to the formula (V):

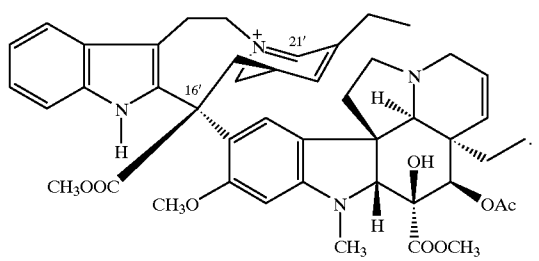

(V)

16. A product (B), of the compound of formula (VI):

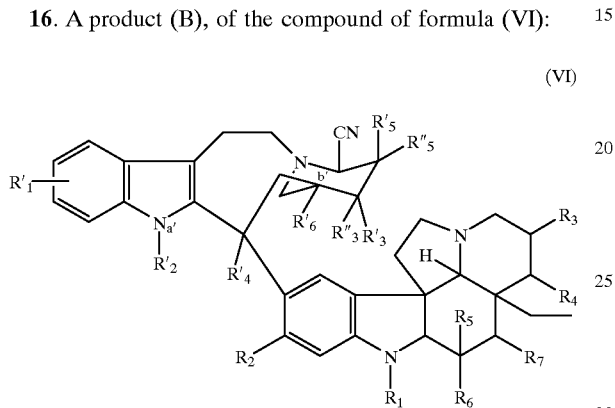

(VI)

in which:
- R'$_1$ represents a hydrogen atom or an alkoxy, acyl, formyl or halogenoacyl group,
- R'$_2$ represents a hydrogen atom or an alkyl group,
- R'$_3$ and R"$_3$ are identical or different and each independently represents a hydrogen atom or a hydroxyl or alkanoyloxyl group, or R'$_3$ and R"$_3$ together form a carbonyl group, or R'$_3$ and R'$_5$ together form a double bond,
- R'$_4$ represents a hydrogen atom or an alkyloxycarbonyl, hydroxymethyl or alkanoyloxymethyl group,
- R'$_5$ and R"$_5$ are identical or different and represent, individually, a hydrogen atom or a hydroxyl, alkanoyloxyl, ethyl or 2-hydroxyethyl group,
- R'$_6$ represents a hydrogen atom or an ethyl, 2-hydroxyethyl or acetyl group,
- R$_1$ represents a hydrogen atom or an alkyl, formyl or acyl group,
- R$_2$ represents a hydrogen atom or an alkoxy group,
- R$_3$ represents a hydrogen atom or a hydroxyl or alkanoyloxyl group, or R$_3$ and R$_4$ together form an epoxy bridge or a double bond,
- R$_4$ represents a hydrogen atom or a hydroxyl or alkanoyloxyl group, or R$_4$ and R$_5$ together form an epoxy bridge,
- R$_6$ represents an alkyloxycarbonyl, hydrazido, acetamido, hydroxymethyl or alkanoyloxymethyl group,
- R$_5$ and R$_7$ represent a hydrogen atom or a hydroxyl or alkanoyloxyl group.

17. The product (B), according to claim 16, wherein R'$_4$ represents an alkyloxycarbonyl group.

18. The product (B), according to claim 16, wherein R$_1$ represents an alkyl group.

19. A product (D) of the formula (VII):

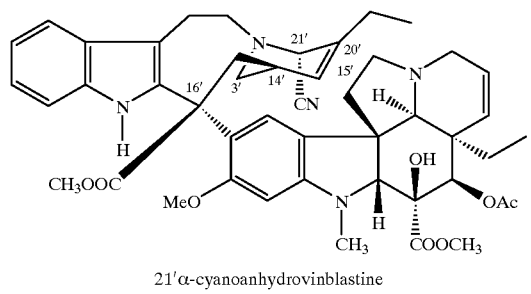

(VII)

21'α-cyanoanhydrovinblastine

20. A process for preparing the product (D) as defined in claim 19, by reacting catharanthine with vindoline, wherein the reaction conditions are chosen so that vindoline is oxidized in order to obtain product (i') of the formula (V) and that the product (i') is subjected to cyanation in order to obtain the product (D).

21. The process according to claim 1, wherein the cyanation step is performed in an organic medium in the presence of a source of cyanide ions which is not alkaline or is slightly alkaline.

22. The process according to claim 20, wherein the cyanation step is performed in an organic medium in the presence of trimethylsilyl cyanide.

23. The process according to claim 22, wherein the cyanation step is performed in an organic medium in the presence of a source of cyanide ions which is not alkaline or is slightly alkaline.

24. The process according to claim 22, wherein the cyanation step is performed in an organic medium in the presence of trimethylsilyl cyanide.

* * * * *